United States Patent [19]
Wideman et al.

[11] Patent Number: 5,684,172
[45] Date of Patent: Nov. 4, 1997

[54] PROCESS FOR THE PREPARATION OF ORGANOSILICON POLYSULFIDE COMPOUNDS

[75] Inventors: Lawson Gibson Wideman, Tallmadge; Theodore Lamson Folk, Cuyahoga Falls; Martin Paul Cohen, Fairlawn, all of Ohio

[73] Assignee: The Goodyear Tire & Rubber Company, Akron, Ohio

[21] Appl. No.: 797,356

[22] Filed: Feb. 11, 1997

[51] Int. Cl.[6] ........................................... C07F 7/08
[52] U.S. Cl. ........................................ 556/427; 548/110
[58] Field of Search .............................. 556/427; 548/110

[56] References Cited

U.S. PATENT DOCUMENTS

| | | | |
|---|---|---|---|
| 5,359,065 | 10/1994 | Krishnamurty | 556/427 X |
| 5,399,739 | 3/1995 | French et al. | 556/427 |
| 5,405,985 | 4/1995 | Parker et al. | 556/427 |
| 5,466,848 | 11/1995 | Childress | 556/427 |
| 5,468,893 | 11/1995 | Parker et al. | 556/427 |
| 5,489,701 | 2/1996 | Childress et al. | 556/427 |
| 5,583,245 | 12/1996 | Parker et al. | 556/427 |

*Primary Examiner*—Paul F. Shaver
*Attorney, Agent, or Firm*—Bruce J. Hendricks

[57] ABSTRACT

The present invention relates to a process for the preparation of organosilicon polysulfide compounds. The process involves reacting a mercaptoalkoxysilane with a benzothiazolyl-morpholinyl disulfide compound.

14 Claims, No Drawings

PROCESS FOR THE PREPARATION OF ORGANOSILICON POLYSULFIDE COMPOUNDS

BACKGROUND OF THE INVENTION

The present invention relates to a process for the preparation of organosilicon polysulfide compounds. Many organosilicon polysulfides are known adhesion promoters in sulfur-vulcanizable rubber mixtures reinforced with inorganic materials such as glass $SiO_2$, aluminosilicates and carbon black.

U.S. Pat. No. 4,820,751 relates to a rubber composition for use in tires containing certain coupling agents. Amongst the number of coupling agents that are disclosed, unsymmetrical coupling agents containing a benzothiazole moiety are included.

U.S. Pat. Nos. 3,842,111, 3,873,489 and 3,978,103 relate to symmetrical sulfur containing organosilicon compounds. Inclusive amongst such compounds are where the sulfur ranges from $S_2$ to $S_6$.

GB 1,484,909 discloses a process for the preparation of organo trialkoxysilane disulfides. In accordance with the teachings of this reference, mercaptopropyl trimethoxy silane or mercaptopropyl triethoxy silane is reacted with sulfuryl chloride in an inert solvent at temperatures of from 0° to 100°. The disulfide is then obtained by fractional distillation. The yields of desired product range in the neighborhood of 63 to 65 percent of theoretical.

U.S. Pat. No. 3,842,111 discloses a method for the preparation of organosilicon disulfide compounds by oxidizing mercaptoalkoxysilanes. Representative oxidizing agents include oxygen, chlorine, halogens of atomic weight 35 to 127, nitric oxide, sulfuryl chloride and sulfoxides.

Generally speaking, organosilicon disulfide compounds are very expensive and, with the increasing interest in silica-reinforced vulcanizable rubber, more cost-efficient methods of preparing these compounds are needed.

SUMMARY OF THE INVENTION

The present invention relates to a process for the preparation of organosilicon polysulfide compounds. The present invention may be used to prepare symmetrical organosilicon polysulfide compounds of the formula:

$$Z-R^1-S_n-R^1-Z, \qquad I$$

unsymmetrical organosilicon polysulfide compounds of the formula

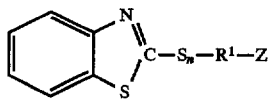

and mixtures thereof wherein Z is selected from the group consisting of

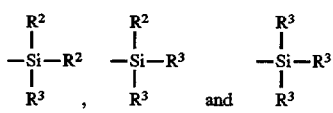

wherein $R^1$ is selected from the group consisting of a substituted or unsubstituted alkylene group having a total of 1 to 18 carbon atoms and a substituted or unsubstituted arylene group having a total of 6 to 12 carbon atoms; and n is an integer of from 2 to 8; $R^2$ may be the same or different and is independently selected from the group consisting of an alkyl group having 1 to 18 carbons and phenyl; $R^3$ may be the same or different and is independently selected from the group consisting of alkoxy groups having 1 to 8 carbon atoms and cycloalkoxy groups with 5 to 8 carbon atoms; and n is an integer of from 2 to 8.

DETAILED DESCRIPTION OF THE INVENTION

There is disclosed a process for the preparation of organosilicon polysulfide compounds comprising reacting (a) the benzothiazolyl-morpholinyl disulfide compound of the formula

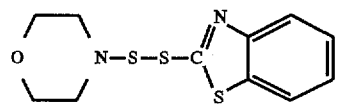

with (b) mercaptoalkoxysilane compound of the formula $$Z-R^1-SH \qquad IV$$

wherein Z is selected from the group consisting of

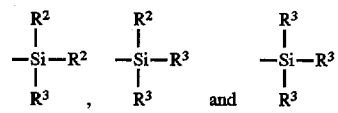

wherein $R^1$ is selected from the group consisting of a substituted or unsubstituted alkylene group having a total of 1 to 18 carbon atoms and a substituted or unsubstituted arylene group having a total of 6 to 12 carbon atoms; $R^2$ may be the same or different and is independently selected from the group consisting of an alkyl group having 1 to 18 carbons and phenyl; $R^3$ may be the same or different and is independently selected from the group consisting of alkoxy groups having 1 to 8 carbon atoms and cycloalkoxy groups with 5 to 8 carbon atoms; and n is an integer of from 2 to 8.

With respect to formulas I and II, preferably $R^1$ is an unsubstituted alkylene group having a total of from 2 to 5 carbon atoms, Z is

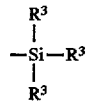

each $R^3$ is an alkoxy group having from 1 to 3 carbon atoms and n is an integer of from 2 to 6.

Similarly, with respect to formula IV, preferably $R^1$ is an unsubstituted alkylene group having a total of from 2 to 5 carbon atoms; z is

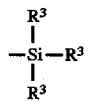

and each $R^3$ is an alkoxy group having from 1 to 3 carbon atoms.

The present invention relates to a process for the preparation of organosilicon polysulfide compounds of formula I and II. Representative organosilicon polysulfide compounds of formula I where n is 2 which may be prepared in accordance with the present invention include 2,2'-bis(trimethoxysilylethyl)disulfide; 3,3'-bis(trimethoxysilylpropyl)disulfide; 3,3'-bis(triethoxysilylpropyl) disulfide; 2,2'-bis(triethoxysilylethyl)disulfide; 2,2'-bis(tripropoxysilylethyl)disulfide; 2,2'-bis(tri-sec-butoxysilylethyl)disulfide; 2,2'-bis(tri-t-butoxysilylethyl)disulfide; 3,3'-bis(triisopropoxysilylpropyl)disulfide; 3,3'-bis(trioctoxysilylpropyl)disulfide; 2,2'-bis[tri(2-ethylhexoxy)silylethyl]disulfide; 2,2'-bis(dimethoxy ethoxysilylethyl)disulfide; 3,3'-bis(methoxyethoxypropoxysilylpropyl)disulfide; 3,3'-bis(dimethoxymethylsilylpropyl)disulfide; 3,3'-bis(methoxy dimethylsilylpropyl)disulfide; 3,3'-bis(diethoxymethylsilylpropyl)disulfide, 3,3'-bis(ethoxy dimethylsilylpropyl)disulfide, 3,3'-bis(cyclohexoxy dimethylsilylpropyl)disulfide; 4,4'-bis(trimethoxysilylbutyl)disulfide; 3,3'-bis(trimethoxysilyl-3-methylpropyl)disulfide; 3,3'-bis(tripropoxysilyl-3-methylpropyl)disulfide; 3,3'-bis(dimethoxy menhylsilyl-3-ethylpropyl)disulfide; 3,3'-bis(trimethoxysilyl-2-methylpropyl)disulfide; 3,3'-bis(dimethoxyphenylsilyl-2-methylpropyl)disulfide; 3,3'-bis(trimethoxysilylcyclohexyl)disulfide; 12,12'-bis(trimethoxysilyldodecyl)disulfide; 12,12'-bis(triethoxysilyldodecyl)disulfide; 18,18'-bis(trimethoxysilyloctadecyl)disulfide; 18,18'-bis(methoxydimethylsilyloctadecyl)disulfide; 2,2'-bis(trimethoxysilyl-2-methylethyl)disulfide; 2,2'-bis(tripropoxysilyl-2-methylethyl)disulfide; 2,2'-bis(trioctoxysilyl-2-methylethyl)disulfide; 2,2'-bis(trimethoxysilyl-phenyl)disulfide; 2,2'-bis(triethoxysilyl-phenyl)disulfide; 2,2'-bis(trimethoxysilyl-tolyl)disulfide; 2,2'-bis(triethoxysilyl-tolyl)disulfide; 2,2'-bis(trimethoxysilyl-methyl tolyl)disulfide; 2,2'-bis(triethoxysilyl-methyl tolyl)disulfide; 2,2'-bis(trimethoxysilyl-ethyl phenyl)disulfide; 2,2'-bis(triethoxysilyl-ethyl phenyl)disulfide; 2,2'-bis(trimethoxysilyl-ethyl tolyl)disulfide; 2,2'-bis(triethoxysilyl-ethyl tolyl)disulfide; 3,3'-bis(trimethoxysilyl-propyl phenyl)disulfide; 3,3'-bis(triethoxysilyl-propyl phenyl)disulfide; 3,3'-bis(trimethoxysilyl-propyl tolyl)disulfide; and 3,3'-bis(triethoxysilyl-propyl tolyl)disulfide.

Representative organosilicon polysulfide compounds of formula I where n is 3 which may be prepared in accordance with the present invention include 2,2'-bis(trimethoxysilylethyl)trisulfide; 3,3'-bis(trimethoxysilylpropyl)trisulfide; 3,3'-bis(triethoxysilylpropyl)trisulfide; 2,2'-bis(tripropoxysilylethyl)trisulfide; 2,2'-bis(triethoxysilylethyl)trisulfide; 2,2'-bis(tri-sec-butoxysilylethyl)trisulfide; 2,2'-bis(tri-t-butoxyethyl)trisulfide; 3,3'-bis(triisopropoxysilylpropyl)trisulfide; 3,3'-bis(trioctoxysilylpropyl)trisulfide; 2,2'-bis[tri(2-ethylhexoxy)silylethyl]trisulfide; 2,2'-bis(dimethoxy ethoxysilylethyl)trisulfide; 3,3'-bis(methoxyethoxypropoxysilylpropyl)trisulfide; 3,3'-bis(dimethoxymethylsilylpropyl)trisulfide; 3,3'-bis(methoxy dimethylsilylpropyl)trisulfide; 3,3'-bis(diethoxymethylsilylpropyl)trisulfide; 3,3'-bis(ethoxy-dimethylsilylpropyl)trisulfide; 3,3'-(cyclohexoxy dimethylsilylpropyl)trisulfide; 4,4'-bis(trimethoxysilylbutyl)trisulfide; 3,3'-bis(trimethoxysilyl-3-methylpropyl)trisulfide; 3,3'-bis(tripropoxysilyl-3-methylpropyl)trisulfide; 3,3'-bis(dimethoxy methylsilyl-3-ethylpropyl)trisulfide; 3,3'-bis(trimethoxysilyl-2-methylpropyl)trisulfide; 3,3'-bis(dimethoxyphenylsilyl-2-methylpropyl)trisulfide; 3,3'-bis(trimethoxysilylcyclohexyl)trisulfide; 12,12'-bis(trimethoxysilyldodecyl)trisulfide; 12,12'-bis(triethoxysilyldodecyl)trisulfide; 18,18'-bis(trimethoxysilyloctadecyl)trisulfide; 18,18'-bis(methoxydimethylsilyloctadecyl)trisulfide; 2,2'-bis(trimethoxysilyl-2-methylethyl)trisulfide; 2,2'-bis(tripropoxysilyl-2-methylethyl)trisulfide; 2,2'-bis(trioctoxysilyl-2-methylethyl)trisulfide; 2,2'-bis(trimethoxysilyl-phenyl)trisulfide; 2,2'-bis(triethoxysilyl-phenyl)trisulfide; 2,2'-bis(trimethoxysilyl-tolyl)trisulfide; 2,2'-bis(triethoxysilyl-tolyl)trisulfide; 2,2'-bis(trimethoxysilyl-methyl tolyl)trisulfide; 2,2'-bis(triethoxysilyl-methyl tolyl)trisulfide; 2,2'-bis(trimethoxysilyl-ethyl phenyl)trisulfide; 2,2'-bis(triethoxysilyl-ethyl phenyl)trisulfide; 2,2'-bis(trimethoxysilyl-ethyl tolyl)trisulfide; 2,2'-bis(triethoxysilyl-ethyl tolyl)trisulfide; 3,3'-bis(trimethoxysilyl-propyl phenyl)trisulfide; 3,3'-bis(triethoxysilyl-propyl phenyl)trisulfide; 3,3'-bis(trimethoxysilyl-propyl tolyl)trisulfide; and 3,3'-bis(triethoxysilyl-propyl tolyl)trisulfide.

Representative organosilicon polysulfide compounds of formula I where n is 4 which may be prepared in accordance with the present invention include 2,2'-bis(trimethoxysilylethyl)tetrasulfide; 3,3'-bis(trimethoxysilylpropyl)tetrasulfide; 3,3'-bis(triethoxysilylpropyl)tetrasulfide; 2,2'-bis(tripropoxysilylethyl)tetrasulfide; 2,2'-bis(triethoxysilylethyl)tetrasulfide; 2,2'-bis(tri-sec-butoxysilylethyl)tetrasulfide; 2,2'-bis(tri-t-butoxyethyl)tetrasulfide; 3,3'-bis(triisopropoxysilylpropyl)tetrasulfide; 3,3'-bis(trioctoxysilylpropyl)tetrasulfide; 2,2'-bis[tri(2-ethylhexoxy)silylethyl]tetrasulfide; 2,2'-bis(dimethoxy ethoxysilylethyl)tetrasulfide; 3,3'-bis(methoxyethoxypropoxysilylpropyl)tetrasulfide; 3,3'-bis(dimethoxymethylsilylpropyl)tetrasulfide; 3,3'-bis(methoxy dimethylsilylpropyl)tetrasulfide; 3,3'-bis(diethoxymethylsilylpropyl)tetrasulfide; 3,3'-bis(ethoxy-dimethylsilylpropyl)tetrasulfide; 3,3'-bis(cyclohexoxy dimethylsilylpropyl)tetrasulfide; 4,4'-bis(trimethoxysilylbutyl)tetrasulfide; 3,3'-bis(trimethoxysilyl-3-methylpropyl)tetrasulfide; 3,3'-bis(tripropoxysilyl-3-methylpropyl)tetrasulfide; 3,3'-bis(dimethoxy methylsilyl-3-ethylpropyl)tetrasulfide; 3,3'-bis(trimethoxysilyl-2-methylpropyl)tetrasulfide; 3,3'-bis(dimethoxyphenylsilyl-2-methylpropyl)tetrasulfide; 3,3'-bis(trimethoxysilylcyclohexyl)tetrasulfide; 12,12'-bis(trimethoxysilyldodecyl)tetrasulfide; 12,12'-bis(triethoxysilyldodecyl)tetrasulfide; 18,18'-bis(trimethoxysilyloctadecyl)tetrasulfide; 18,18'-bis(methoxydimethylsilyloctadecyl)tetrasulfide; 2,2'-bis(trimethoxysilyl-2-methylethyl)tetrasulfide; 2,2'-bis(tripropoxysilyl-2-methylethyl)tetrasulfide; 2,2'-bis(trioctoxysilyl-2-methylethyl)tetrasulfide; 2,2'-bis(trimethoxysilyl-phenyl)tetrasulfide; 2,2'-bis(triethoxysilyl-phenyl)tetrasulfide; 2,2'-bis(trimethoxysilyl-tolyl)tetrasulfide; 2,2'-bis(triethoxysilyl-tolyl)tetrasulfide; 2,2'-bis(trimethoxysilyl-methyl tolyl)tetrasulfide; 2,2'-bis(triethoxysilyl-methyl tolyl)tetrasulfide; 2,2 -bis(trimethoxysilyl-ethyl phenyl)tetrasulfide; 2,2'-bis(triethoxysilyl-ethyl phenyl)tetrasulfide; 2,2'-bis(trimethoxysilyl-ethyl tolyl)tetrasulfide; 2,2'-bis(triethoxysilyl-ethyl tolyl)tetrasulfide; 3,3'-bis(trimethoxysilyl-propyl phenyl)tetrasulfide; 3,3'-bis(triethoxysilyl-propyl phenyl)tetrasulfide; 3,3'-bis(trimethoxysilyl-propyl tolyl)tetrasulfide; and 3,3'-bis(triethoxysilyl-propyl tolyl)tetrasulfide.

Representative of organosilicon polysulfide compounds of formula I when n is 5 which may be prepared in accordance with the present invention include 2,2'-bis (trimethoxysilylethyl)pentasulfide; 3,3'-bis (trimethoxysilylpropyl)pentasulfide; 3,3'-bis (triethoxysilylpropyl)pentasulfide; 2,2'-bis (tripropoxysilylethyl)pentasulfide; 2,2'-bis (triethoxysilylethyl)pentasulfide; 2,2'-bis(tri-sec-butoxysilylethyl)pentasulfide; 2,2'-bis(tri-t-butoxyethyl) pentasulfide; 3,3'-bis(triisopropoxysilylpropyl)pentasulfide; 3,3'-bis(trioctoxysilylpropyl)pentasulfide; 2,2'-bis[tri(2-ethylhexoxy)silylethyl]pentasulfide; 2,2'-bis(dimethoxy ethoxysilylethyl)pentasulfide; 3,3'-bis (methoxyethoxypropoxysilylpropyl)pentasulfide; 3,3'-bis (dimethoxymethylsilylpropyl)pentasulfide; 3,3'-bis (methoxy dimethylsilylpropyl)pentasulfide; 3,3'-bis (diethoxymethylsilylpropyl)pentasulfide; 3,3'-bis(ethoxy-dimethylsilylpropyl)pentasulfide; 3,3'-bis(cyclohexoxy dimethylsilylpropyl)pentasulfide; 4,4'-bis (trimethoxysilylbutyl)pentasulfide; 3,3'-bis(trimethoxysilyl-3-methylpropyl)pentasulfide; 3,3'-bis(tripropoxysilyl-3-methylpropyl)pentasulfide; 3,3'-bis(dimethoxy methylsilyl-3-ethylpropyl)pentasulfide; 3,3'-bis(trimethoxysilyl-2-methylpropyl)pentasulfide; 3,3'-bis(dimethoxyphenylsilyl-2-methylpropyl)pentasulfide; 3,3'-bis (trimethoxysilylcyclohexyl)pentasulfide; 12,12'-bis (trimethoxysilyldodecyl)pentasulfide; 12,12'-bis (triethoxysilyldodecyl)pentasulfide; 18,18'-bis (trimethoxysilyloctadecyl)pentasulfide; 18,18'-bis (methoxydimethylsilyloctadecyl)pentasulfide; 2,2'-bis (trimethoxysilyl-2-methylethyl)pentasulfide; 2,2'-bis (tripropoxysilyl-2-methylethyl)pentasulfide; 2,2'-bis (trioctoxysilyl-2-methylethyl)pentasulfide; 2,2'-bis (trimethoxysilyl-phenyl)pentasulfide; 2,2'-bis (triethoxysilyl-phenyl)pentasulfide; 2,2'-bis (trimethoxysilyl-tolyl)pentasulfide; 2,2'-bis(triethoxysilyl-tolyl)pentasulfide; 2,2'-bis(trimepeoxysilyl-methyl tolyl) pentasulfide; 2,2'-bis(triethoxysilyl-methyl tolyl) pentasulfide; 2,2'-bis(trimethoxysilyl-ethyl phenyl) pentasulfide; 2,2'-bis(triethoxysilyl-ethyl phenyl) pentasulfide; 2,2'-bis(trimethoxysilyl-ethyl tolyl) pentasulfide; 2,2'-bis(triethoxysilyl-ethyl tolyl)pentasulfide; 3,3'-bis(trimethoxysilyl-propyl phenyl)pentasulfide; 3,3'-bis (triethoxysilyl-propyl phenyl)pentasulfide; 3,3'-bis (trimethoxysilyl-propyl tolyl)pentasulfide; and 3,3'-bis (triethoxysilyl-propyl tolyl)pentasulfide.

Representative of organosilicon polysulfide compounds of formula I where n is 6 which may be prepared in accordance with the present invention include 2,2'-bis (trimethoxysilylethyl)hexasulfide; 3,3'-bis (trimethoxysilylpropyl)hexasulfide; 3,3'-bis (triethoxysilylpropyl)hexasulfide; 2,2'-bis (tripropoxysilylethyl)hexasulfide; 2,2'-bis (triethoxysilylethyl)hexasulfide; 2,2'-bis(tri-sec-butoxysilylethyl)hexasulfide; 2,2'-bis(tri-t-butoxysilylethyl) hexasulfide; 3,3'-bis(triisopropoxysilylpropyl)hexasulfide; 3,3'-bis(trioctoxysilylpropyl)hexasulfide; 2,2'-bis[tri(2-ethylhexoxy)silylethyl]hexasulfide; 2,2'-bis(dimethoxy ethoxysilylethyl)hexasulfide; 3,3'-bis (methoxyethoxypropoxysilylpropyl)hexasulfide; 3,3'-bis (dimethoxymethylsilylpropyl)hexasulfide; 3,3'-bis(methoxy dimethylsilylpropyl)hexasulfide; 3,3'-bis (diethoxymethylsilylpropyl)hexasulfide; 3,3'-bis(ethoxy-dimethylsilylpropyl)hexasulfide; 3,3'-bis(cyclohexoxy dimethylsilylpropyl)hexasulfide; 4,4'-bis (trimethoxysilylbutyl)hexasulfide; 3,3'-bis(trimethoxysilyl-3-methylpropyl)hexasulfide; 3,3'-bis(tripropoxysilyl-3-methylpropyl)hexasulfide; 3,3'-bis(dimethoxy methylsilyl-3-ethylpropyl)hexasulfide; 3,3'-bis(trimethoxysilyl-2-methylpropyl)hexasulfide; 3,3'-bis(dimethoxyphenylsilyl-2-methylpropyl)hexasulfide; 3,3'-bis (trimethoxysilylcyclohexyl)hexasulfide; 12,12'-bis (trimethoxysilyldodecyl)hexasulfide; 12,12'-bis (triethoxysilyldodecyl)hexasulfide; 18,18'-bis (trimethoxysilyloctadecyl)hexasulfide; 18,18'-bis (methoxydimethylsilyloctadecyl)hexasulfide; 2,2'-bis (trimethoxysilyl-2-methylethyl)hexasulfide; 2,2'-bis (tripropoxysilyl-2-methylethyl)hexasulfide; 2,2'-bis (trioctoxysilyl-2-methylethyl)hexasulfide; 2,2'-bis (trimethoxysilyl-phenyl)hexasulfide; 2,2'-bis(triethoxysilyl-phenyl)hexasulfide; 2,2'-bis(trimethoxysilyl-tolyl) hexasulfide; 2,2'-bis(triethoxysilyl-tolyl)hexasulfide; 2,2'-bis(trimethoxysilyl-methyl tolyl)hexasulfide; 2,2'-bis (triethoxysilyl-methyl tolyl)hexasulfide; 2,2'-bis (trimethoxysilyl-ethyl phenyl)hexasulfide; 2,2'-bis (triethoxysilyl-ethyl phenyl)hexasulfide; 2,2'-bis (trimethoxysilyl-ethyl tolyl)hexasulfide; 2,2'-bis (triethoxysilyl-ethyl tolyl)hexasulfide; 3,3'-bis (trimethoxysilyl-propyl phenyl)hexasulfide; 3,3'-bis (triethoxysilyl-propyl phenyl)hexasulfide; 3,3'-bis (trimethoxysilyl-propyl tolyl)hexasulfide; and 3,3'-bis (triethoxysilyl-propyl tolyl)hexasulfide.

Representative organosilicon polysulfide compounds of formula I where n is 7 which may be prepared in accordance with the present invention include 2,2'-bis (trimethoxysilylethyl)heptasulfide; 3,3'-bis (trimethoxysilylpropyl)heptasulfide; 3,3'-bis (triethoxysilylpropyl)heptasulfide; 2,2'-bis (tripropoxysilylethyl)heptasulfide; 2,2'-bis (triethoxysilylethyl)heptasulfide; 2,2'-bis(tri-sec-butoxysilylethyl)heptasulfide; 2,2'-bis(tri-t-butoxysilylethyl)heptasulfide; 3,3'-bis (triisopropoxysilylpropyl)heptasulfide; 3,3'-bis (trioctoxysilylpropyl)heptasulfide; 2,2'-bis[tri(2-ethylhexoxy)silylethyl]heptasulfide; 2,2'-bis(dimethoxy ethoxysilylethyl)heptasulfide; 3,3'-bis (methoxyethoxypropoxysilylpropyl)heptasulfide; 3,3'-bis (dimethoxymethylsilylpropyl)heptasulfide; 3,3'-bis (methoxy dimethylsilylpropyl)heptasulfide; 3,3'-bis (diethoxymethylsilylpropyl)heptasulfide; 3,3'-bis(ethoxy-dimethylsilylpropyl)heptasulfide; 3,3'-bis(cyclohexoxy dimethylsilylpropyl)heptasulfide; 4,4'-bis (trimethoxysilylbutyl)heptasulfide; 3,3'-bis(trimethoxysilyl-3-methylpropyl)heptasulfide; 3,3'-bis(tripropoxysilyl-3-methylpropyl)heptasulfide; 3,3'-bis(dimethoxy methylsilyl-3-ethylpropyl)heptasulfide; 3,3'-bis(trimethoxysilyl-2-methylpropyl)heptasulfide; 3,3'-bis(dimethoxyphenylsilyl-2-methylpropyl)heptasulfide; 3,3'-bis (trimethoxysilylcyclohexyl)heptasulfide; 12,12'-bis (trimethoxysilyldodecyl)heptasulfide; 12,12'-bis (triethoxysilyldodecyl)heptasulfide; 18,18'-bis (trimethoxysilyloctadecyl)heptasulfide; 18,18'-bis (methoxydimethylsilyloctadecyl)heptasulfide; 2,2'-bis (trimethoxysilyl-2-methylethyl)heptasulfide; 2,2'-bis (tripropoxysilyl-2-methylethyl)heptasulfide; 2,2'-bis (trioctoxysilyl-2-methylethyl)heptasulfide; 2,2'-bis (trimethoxysilyl-phenyl)heptasulfide; 2,2'-bis (triethoxysilyl-phenyl)heptasulfide; 2,2'-bis (trimethoxysilyl-tolyl)heptasulfide; 2,2'-bis(triethoxysilyl-tolyl)heptasulfide; 2,2'-bis(trimethoxysilyl-methyl tolyl) heptasulfide; 2,2'-bis(triethoxysilyl-methyl tolyl) heptasulfide; 2,2'-bis(trimethoxysilyl-ethyl phenyl) heptasulfide; 2,2'-bis(triethoxysilyl-ethyl phenyl) heptasulfide; 2,2'-bis(trimethoxysilyl-ethyl tolyl) heptasulfide; 2,2'-bis(triethoxysilyl-ethyl tolyl)heptasulfide; 3,3'-bis(trimethoxysilyl-propyl phenyl)heptasulfide; 3,3'-bis (triethoxysilyl-propyl phenyl)heptasulfide; 3,3'-bis (trimethoxysilyl-propyl tolyl)heptasulfide; and 3,3'-bis (triethoxysilyl-propyl tolyl)heptasulfide.

Representative organosilicon polysulfide compounds of formula I where n is 8 which may be prepared in accordance with the present invention include 2,2'-bis (trimethoxysilylethyl)octasulfide; 3,3'-bis (trimethoxysilylpropyl)octasulfide; 3,3-bis (triethoxysilylpropyl)octasulfide; 2,2'-bis (tripropoxysilylethyl)octasulfide; 2,2'-bis (triethoxysilylethyl)octasulfide; 2,2'-bis(tri-sec-butoxysilylethyl)octasulfide; 2,2'-bis(tri-t-butoxysilylethyl) octasulfide; 3,3'-bis(triisopropoxysilylpropyl)octasulfide; 3,3'-bis(trioctoxysilylpropyl)octasulfide; 2,2'-bis[tri(2-ethylhexoxy)silylethyl]octasulfide; 2,2'-bis(dimethoxy ethoxysilylethyl)octasulfide; 3,3'-bis (methoxyethoxypropoxysilylpropyl)octasulfide; 3,3'-bis (dimethoxymethylsilylpropyl)octasulfide; 3,3'-bis(methoxy dimethylsilylpropyl)octasulfide; 3,3'-bis (diethoxymethylsilylpropyl)octasulfide; 3,3'-bis(ethoxy-dimethylsilylpropyl)octasulfide; 3,3'-bis(cyclohexoxy dimethylsilylpropyl)octasulfide; 4,4'-bis (trimethoxysilylbutyl)octasulfide; 3,3'-bis(trimethoxysilyl-3-methylpropyl)octasulfide; 3,3'-bis(tripropoxysilyl-3-methylpropyl)octasulfide; 3,3'-bis(dimethoxy methylsilyl-3-ethylpropyl)octasulfide; 3,3'-bis(trimethoxysilyl-2-methylpropyl)octasulfide; 3,3'-bis(dimethoxyphenylsilyl-2-methylpropyl)octasulfide; 3,3'-bis (trimethoxysilylcyclohexyl)octasulfide; 12,12'-bis (trimethoxysilyldodecyl)octasulfide; 12,12'-bis (triethoxysilyldodecyl)octasulfide; 18,18'-bis (trimethoxysilyloctadecyl)octasulfide; 18,18'-bis (methoxydimethylsilyloctadecyl)octasulfide; 2,2'-bis (trimethoxysilyl-2-methylethyl)octasulfide; 2,2'-bis (tripropoxysilyl-2-methylethyl)octasulfide; 2,2'-bis (trioctoxysilyl-2-methylethyl)octasulfide; 2,2'-bis (trimethoxysilyl-phenyl)octasulfide; 2,2'-bis(triethoxysilyl-phenyl)octasulfide; 2,2'-bis(trimethoxysilyl-tolyl) octasulfide; 2,2'-bis(triethoxysilyl-tolyl)octasulfide; 2,2'-bis (trimethoxysilyl-methyl tolyl)octasulfide; 2,2'-bis (triethoxysilyl-methyl tolyl)octasulfide; 2,2'-bis (trimethoxysilyl-ethyl phenyl)octasulfide; 2,2'-bis (triethoxysilyl-ethyl phenyl)octasulfide; 2,2'-bis (trimethoxysilyl-ethyl tolyl)octasulfide; 2,2'-bis (triethoxysilyl-ethyl tolyl)octasulfide; 3,3'-bis (trimethoxysilyl-propyl phenyl)octasulfide; 3,3'-bis (triethoxysilyl-propyl phenyl)octasulfide; 3,3'-bis (trimethoxysilyl-propyl tolyl)octasulfide; and 3,3'-bis (triethoxysilyl-propyl tolyl)octasulfide.

Representative organosilicon polysulfide compounds of formula II where n is 2 which may be prepared in accordance with the present invention include 2-benzothiazolyl-(3-triethoxysilylpropyl)disulfide; 2-benzothiazolyl-(2-trimethoxysilylethyl)disulfide; 2-benzothiazolyl-(3-trimethoxysilylpropyl)disulfide; 2-benzothiazolyl-(2-triethoxysilylpropyl)disulfide; 2-benzothiazolyl-(3-triethoxysilylpropyl)disulfide; 2-benzothiazolyl-(2-tripropoxysilylethyl)disulfide; 2-benzothiazolyl-(2-tri-sec-butoxysilylethyl)disulfide; 2-benzothiazolyl-(3-tri-t-butoxysilylethyl)disulfide; 2-benzothiazolyl-(3-triisopropoxysilylpropyl)disulfide; 2-benzothiazolyl-(3-trioctoxysilylpropyl)disulfide; 2-benzothiazolyl-2-[tri(2-ethylhexoxy)silylethyl]disulfide; 2-benzothiazolyl-(2-dimethoxy ethoxysilylethyl)disulfide; 2-benzothiazolyl-(3-methoxyethoxypropoxysilylpropyl)disulfide; 2-benzothiazolyl-(3-dimethoxymethylsilylpropyl)disulfide; 2-benzothiazolyl-(3-methoxy dimethylsilylpropyl)disulfide; 2-benzothiazolyl-(3-diethoxymethyl-silylpropyl)disulfide; 2-benzothiazolyl-(3-ethoxydimethylsilylpropyl)disulfide; 2-benzothiazolyl-(3-cyclohexoxy dimethylsilylpropyl) disulfide; 2-benzothiazolyl-(4-trimethoxysilylbutyl) disulfide; 2-benzothiazolyl-(3-trimethoxysilyl-3-methylpropyl)disulfide; 2-benzothiazolyl-(3-tripropoxysilyl-3-methylpropyl)disulfide; 2-benzothiazolyl-(3-dimethoxy methylsilyl-3-ethylpropyl)disulfide; 2-benzothiazolyl-(3-trimethoxysilyl-2-methylpropyl) disulfide; 2-benzothiazolyl-(3-dimethoxyphenylsilyl-2-methylpropyl)disulfide; 2-benzothiazolyl-(3-trimethoxysilylcyclohexyl)disulfide; 2-benzothiazolyl-(12-trimethoxysilyldodecyl)disulfide; 2-benzothiazolyl-(12-triethoxysilyldodecyl)disulfide; 2-benzothiazolyl-(18-trimethoxysilyloctadecyl)disulfide; 2-benzothiazolyl-(18-methoxydimethylsilyloctadecyl)disulfide; 2-benzothiazolyl-(2-trimethoxysilyl-2-methylethyl)disulfide; 2-benzothiazolyl-(2-tripropoxysilyl-2-methylethyl) disulfide; 2-benzothiazolyl-(2-trioctoxysilyl-2-methylethyl) disulfide; 2-benzothiazolyl-(2-trimethoxysilyl-phenyl) disulfide; 2-benzothiazolyl-(2-triethoxysilyl-phenyl) disulfide; 2-benzothiazolyl-(2-trimethoxysilyl-tolyl) disulfide; 2-benzothiazolyl-(2-triethoxysilyl-tolyl)disulfide; 2-benzothiazolyl-(2-trimethoxysilyl-methyl tolyl)disulfide; 2-benzothiazolyl-(2-triethoxysilyl-methyl tolyl)disulfide; 2-benzothiazolyl-(2-trimethoxysilyl-ethyl phenyl)disulfide; 2-benzothiazolyl-(2-triethoxysilyl-ethyl phenyl)disulfide; 2-benzothiazolyl-(2-trimethoxysilyl-ethyl tolyl)disulfide; 2-benzothiazolyl-(2-triethoxysilyl-ethyl tolyl)disulfide; 2-benzothiazolyl-(3-trimethoxysilyl-propyl phenyl) disulfide; 2-benzothiazolyl-(3-triethoxysilyl-propyl phenyl) disulfide; 2-benzothiazolyl-(3-trimethoxysilyl-propyl tolyl) disulfide; and 2-benzothiazolyl-(3-triethoxysilyl-propyl tolyl)disulfide.

Representative organosilicon polysulfide compounds of formula II where n is 3 which may be prepared in accordance with the present invention include 2-benzothiazolyl-(3-triethoxysilylpropyl)trisulfide; 2-benzothiazolyl-(2-trimethoxysilylethyl)trisulfide; 2-benzothiazolyl-(3-trimethoxysilylpropyl)trisulfide; 2-benzothiazolyl-(2-triethoxysilylpropyl)trisulfide; 2-benzothiazolyl-(3-triethoxysilylpropyl)trisulfide; 2-benzothiazolyl-(2-tripropoxysilylethyl)trisulfide; 2-benzothiazolyl-(2-tri-sec-butoxysilylethyl)trisulfide; 2-benzothiazolyl-(3-tri-t-butoxysilylethyl)trisulfide; 2-benzothiazolyl-(3-triisopropoxysilylpropyl)trisulfide; 2-benzothiazolyl-(3-trioctoxysilylpropyl)trisulfide; 2-benzothiazolyl-2-[tri(2-ethylhexoxy)silylethyl]trisulfide; 2-benzothiazolyl-(2-dimethoxy ethoxysilylethyl)trisulfide; 2-benzothiazolyl-(2-methoxyethoxypropoxysilylpropyl)trisulfide; 2-benzothiazolyl-(3-dimethoxymethylsilylpropyl)trisulfide; 2-benzothiazolyl-(3-methoxy dimethylsilylpropyl)trisulfide; 2-benzothiazolyl-(3-diethoxymethyl-silylpropyl)trisulfide; 2-benzothiazolyl-(3-ethoxydimethylsilylpropyl)trisulfide; 2-benzothiazolyl-(3-cyclohexoxy dimethylsilylpropyl) trisulfide; 2-benzothiazolyl-(4-trimethoxysilylbutyl) trisulfide; 2-benzothiazolyl-(3-trimethoxysilyl-3-methylpropyl)trisulfide; 2-benzothiazolyl-(3-tripropoxysilyl-3-methylpropyl)trisulfide; 2-benzothiazolyl-(3-dimethoxy methylsilyl-3-ethylpropyl)trisulfide; 2-benzothiazolyl-(3-trimethoxysilyl-2-methylpropyl) trisulfide; 2-benzothiazolyl-(3-dimethoxyphenylsilyl-2-methylpropyl)trisulfide; 2-benzothiazolyl-(3-trimethoxysilylcyclohexyl)trisulfide; 2-benzothiazolyl-(12-trimethoxysilyldodecyl)trisulfide; 2-benzothiazolyl-(12-triethoxysilyldodecyl)trisulfide; 2-benzothiazolyl-(18-trimethoxysilyloctadecyl)trisulfide; 2-benzothiazolyl-(18- methoxydimethylsilyloctadecyl)trisulfide; 2-benzothiazolyl-(2-trimethoxysilyl-2-methylethyl) trisulfide; 2-benzothiazolyl-(2-tripropoxysilyl-2-methylethyl)trisulfide; 2-benzothiazolyl-(2-trioctoxysilyl-2-methylethyl)trisulfide; 2-benzothiazolyl-(2-trimethoxysilyl-phenyl)trisulfide; 2-benzothiazolyl-(2-triethoxysilylophenyl)trisulfide; 2-benzothiazolyl-(2-trimethoxysilyl-tolyl)trisulfide; 2-benzothiazolyl-(2-triethoxysilyl-tolyl)trisulfide; 2-benzothiazolyl-(2-trimethoxysilyl-methyl tolyl)trisulfide; 2-benzothiazolyl-(2-triethoxysilyl-methyl tolyl)trisulfide; 2-benzothiazolyl-(2-trimethoxysilyl-ethyl phenyl)trisulfide; 2-benzothiazolyl-(2-triethoxysilyl-ethyl phenyl)trisulfide; 2-benzothiazolyl-(2-trimethoxysilyl-ethyl tolyl)trisulfide; 2-benzothiazolyl-(2-triethoxysilyl-ethyl tolyl)trisulfide; 2-benzothiazolyl-(3-trimethoxysilyl-propyl phenyl)trisulfide; 2-benzothiazolyl-(3-triethoxysilyl-propyl phenyl)trisulfide; 2-benzothiazolyl-(3-trimethoxysilyl-propyl tolyl)trisulfide; and 2-benzothiazolyl-(3-triethoxysilyl-propyl tolyl)trisulfide.

Representative organosilicon polysulfide compounds of formula II were n is 4 which may be prepared in accordance with the present invention include 2-benzothiazolyl-(3-triethoxysilylpropyl)tetrasulfide; 2-benzothiazolyl-(2-trimethoxysilylethyl)tetrasulfide; 2-benzothiazolyl-(3-trimethoxysilylpropyl)tetrasulfide; 2-benzothiazolyl-(2-triethoxysilylpropyl)tetrasulfide; 2-benzothiazolyl-(3-triethoxysilylpropyl)tetrasulfide; 2-benzothiazolyl-(2-tripropoxysilylethyl)tetrasulfide; 2-benzothiazolyl-(2-tri-sec-butoxysilylethyl)tetrasulfide; 2-benzothiazolyl-(3-tri-t-butoxysilylethyl)tetrasulfide; 2-benzothiazolyl-(3-triisopropoxysilylpropyl)tetrasulfide; 2-benzothiazolyl-(3-trioctoxysilylpropyl)tetrasulfide; 2-benzothiazolyl-2-[tri(2-ethylhexoxy)silylethyl]tetrasulfide; 2-benzothiazolyl-(2-dimethoxy ethoxysilylethyl)tetrasulfide; 2-benzothiazolyl-(3-methoxyethoxypropoxysilylpropyl)tetrasulfide; 2-benzothiazolyl-(3-dimethoxymethylsilylpropyl) tetrasulfide; 2-benzothiazolyl-(3-methoxy dimethylsilylpropyl)tetrasulfide; 2-benzothiazolyl-(3-diethoxymethyl-silylpropyl)tetrasulfide; 2-benzothiazolyl-(3-ethoxydimethylsilylpropyl)tetrasulfide; 2-benzothiazolyl-(3-cyclohexoxy dimethylsilylpropyl) tetrasulfide; 2-benzothiazolyl-(4-trimethoxysilylbutyl) tetrasulfide; 2-benzothiazolyl-(3-trimethoxysilyl-3-methylpropyl)tetrasulfide; 2-benzothiazolyl-(3-tripropoxysilyl-3-methylpropyl)tetrasulfide; 2-benzothiazolyl-(3-dimethoxy methylsilyl-3-ethylpropyl)tetrasulfide; 2-benzothiazolyl-(3-trimethoxysilyl-2-methylpropyl)tetrasulfide; 2-benzothiazolyl-(3-dimethoxyphenylsilyl-2-methylpropyl)tetrasulfide; 2-benzothiazolyl-(3-trimethoxysilylcyclohexyl)tetrasulfide; 2-benzothiazolyl-(12-trimethoxysilyldodecyl)tetrasulfide; 2-benzothiazolyl-(12-triethoxysilyldodecyl)tetrasulfide; 2-benzothiazolyl-(18-trimethoxysilyloctadecyl)tetrasulfide; 2-benzothiazolyl-(18-methoxydimethylsilyloctadecyl)tetrasulfide; 2-benzothiazolyl-(2-trimethoxysilyl-2-methylethyl)tetrasulfide; 2-benzothiazolyl-(2-tripropoxysilyl-2-methylethyl)tetrasulfide; 2-benzothiazolyl-(2-trioctoxysilyl-2-methylethyl)tetrasulfide; 2-benzothiazolyl-(2-trimethoxysilyl-phenyl) tetrasulfide; 2-benzothiazolyl-(2-triethoxysilyl-phenyl) tetrasulfide; 2-benzothiazolyl-(2-trimethoxysilyl-tolyl) tetrasulfide; 2-benzothiazolyl-(2-triethoxysilyl-tolyl) tetrasulfide; 2-benzothiazolyl-(2-trimethoxysilyl-methyl tolyl)tetrasulfide; 2-benzothiazolyl-(2-triethoxysilyl-methyl tolyl)tetrasulfide; 2-benzothiazolyl-(2-trimethoxysilyl-ethyl phenyl)tetrasulfide; 2-benzothiazolyl-(2-triethoxysilyl-ethyl phenyl)tetrasulfide; 2-benzothiazolyl-(2-trimethoxysilyl-ethyl tolyl)tetrasulfide; 2-benzothiazolyl-(2-triethoxysilyl-ethyl tolyl)tetrasulfide; 2-benzothiazolyl-(3-trimethoxysilyl-propyl phenyl)tetrasulfide; 2-benzothiazolylo(3-triethoxysilyl-propyl phenyl)tetrasulfide; 2-benzothiazolyl-(3-trimethoxysilyl-propyl tolyl)tetrasulfide; and 2-benzothiazolyl-(3-triethoxysilyl-propyl tolyl)tetrasulfide.

Representative organosilicon polysulfide compounds of formula II where n is 5 which may be prepared in accordance with the present invention include 2-benzothiazolyl-(3-triethoxysilylpropyl) pentasulfide; 2-benzothiazolyl-(2-trimethoxysilylethyl)pentasulfide; 2-benzothiazolyl-(3-trimethoxysilylpropyl)pentasulfide; 2-benzothiazolyl-(2-triethoxysilylpropyl)pentasulfide; 2-benzothiazolyl-(3-triethoxysilylpropyl)pentasulfide; 2-benzothiazolyl-(2-tripropoxysilylethyl)pentasulfide; 2-benzothiazolyl-(2-tri-sec-butoxysilylethyl)pentasulfide; 2-benzothiazolyl-(3-tri-t-butoxysilylethyl)pentasulfide; 2-benzothiazolyl-(3-triisopropoxysilylpropyl)pentasulfide; 2-benzothiazolyl-(3-trioctoxysilylpropyl)pentasulfide; 2-benzothiazolyl-2-[tri(2-ethylhexoxy)silylethyl]pentasulfide; 2-benzothiazolyl-(2-dimethoxy ethoxysilylethyl)pentasulfide; 2-benzothiazolyl-(3-methoxyethoxypropoxysilylpropyl)pentasulfide; 2-benzothiazolyl-(3-dimethoxymethylsilylpropyl) pentasulfide; 2-benzothiazolyl-(3-methoxy dimethylsilylpropyl)pentasulfide; 2-benzothiazolyl-(3-diethoxymethyl-silylpropyl)pentasulfide; 2-benzothiazolyl-(3-ethoxydimethylsilylpropyl)pentasulfide; 2-benzothiazolyl-(3-cyclohexoxy dimethylsilylpropyl) pentasulfide; 2-benzothiazolyl-(4-trimethoxysilylbutyl) pentasulfide; 2-benzothiazolyl-(3-trimethoxysilyl-3-methylpropyl)pentasulfide; 2-benzothiazolyl-(3-tripropoxysilyl-3-methylpropyl)pentasulfide; 2-benzothiazolyl-(3-dimethoxy methylsilyl-3-ethylpropyl) pentasulfide; 2-benzothiazolyl-(3-trimethoxysilyl-2-methylpropyl)pentasulfide; 2-benzothiazolyl-(3-dimethoxyphenylsilyl-2-methylpropyl)pentasulfide; 2-benzothiazolyl-(3-trimethoxysilylcyclohexyl) pentasulfide; 2-benzothiazolyl-(12-trimethoxysilyldodecyl) pentasulfide; 2-benzothiazolyl-(12-triethoxysilyldodecyl) pentasulfide; 2-benzothiazolyl-(18-trimethoxysilyloctadecyl)pentasulfide; 2-benzothiazolyl-(18-methoxydimethylsilyloctadecyl)pentasulfide; 2-benzothiazolyl-(2-trimethoxysilyl-2-methylethyl) pentasulfide; 2-benzothiazolyl-(2-tripropoxysilyl-2-methylethyl)pentasulfide; 2-benzothiazolyl-(2-trioctoxysilyl-2-methylethyl)pentasulfide; 2-benzothiazolyl-(2-trimethoxysilyl-phenyl)pentasulfide; 2-benzothiazolyl-(2-triethoxysilyl-phenyl)pentasulfide; 2-benzothiazolyl-(2-trimethoxysilyl-tolyl)pentasulfide; 2-benzothiazolyl-(2-triethoxysilyl-tolyl)pentasulfide; 2-benzothiazolyl-(2-trimethoxysilyl-methyl tolyl)pentasulfide; 2-benzothiazolyl-(2-triethoxysilyl-methyl tolyl)pentasulfide; 2-benzothiazolyl-(2-trimethoxysilyl-ethyl phenyl) pentasulfide; 2-benzothiazolyl-(2-triethoxysilyl-ethyl phenyl)pentasulfide; 2-benzothiazolyl-(2-trimethoxysilyl-ethyl tolyl)pentasulfide; 2-benzothiazolyl-(2-triethoxysilyl-ethyl tolyl)pentasulfide; 2-benzothiazolyl-(3-trimethoxysilyl-propyl phenyl)pentasulfide; 2-benzothiazolyl-(3-triethoxysilyl-propyl phenyl) pentasulfide; 2-benzothiazolyl-(3-trimethoxysilyl-propyl tolyl)pentasulfide; and 2-benzothiazolyl-(3-triethoxysilyl-propyl tolyl)pentasulfide.

Representative organosilicon polysulfide compounds of formula II where n is 6 which may be prepared in accordance with the present invention include 2-benzothiazolyl-(3-triethoxysilylpropyl)hexasulfide; 2-benzothiazolyl-(2-trimethoxysilylethyl)hexasulfide; 2-benzothiazolyl-(3- trimethoxysilylpropyl)hexasulfide; 2-benzothiazolyl-(2-triethoxysilylpropyl)hexasulfide; 2-benzothiazolyl-(3-triethoxysilylpropyl)hexasulfide; 2-benzothiazolyl-(2-tripropoxysilylethyl)hexasulfide; 2-benzothiazolyl-(2-tri-sec-butoxysilylethyl)hexasulfide; 2-benzothiazolyl-(3-tri-t-butoxysilylethyl)hexasulfide; 2-benzothiazolyl-(3-triisopropoxysilylpropyl)hexasulfide; 2-benzothiazolyl-(3-trioctoxysilylpropyl)hexasulfide; 2-benzothiazolyl-2-[tri(2-ethylhexoxy)silylethyl]hexasulfide; 2-benzothiazolyl-(2-dimethoxy ethoxysilylethyl)hexasulfide; 2-benzothiazolyl-(3-methoxyethoxypropoxysilylpropyl)hexasulfide; 2-benzothiazolyl-(3-dimethoxymethylsilylpropyl)hexasulfide; 2-benzothiazolyl-(3-methoxy dimethylsilylpropyl)hexasulfide; 2-benzothiazolyl-(3-diethoxymethyl-silylpropyl)hexasulfide; 2-benzothiazolyl-(3-ethoxydimethylsilylpropyl)hexasulfide; 2-benzothiazolyl-(3-cyclohexoxy dimethylsilylpropyl)hexasulfide; 2-benzothiazolyl-(4-trimethoxysilylbutyl)hexasulfide; 2-benzothiazolyl-(3-trimethoxysilyl-3-methylpropyl)hexasulfide; 2-benzothiazolyl-(3-tripropoxysilyl-3-methylpropyl)hexasulfide; 2-benzothiazolyl-(3-dimethoxy methylsilyl-3-ethylpropyl)hexasulfide; 2-benzothiazolyl-(3-trimethoxysilyl-2-methylpropyl)hexasulfide; 2-benzothiazolyl-(3-dimethoxyphenylsilyl-2-methylpropyl)hexasulfide; 2-benzothiazolyl-(3-trimethoxysilylcyclohexyl)hexasulfide; 2-benzothiazolyl-(12-trimethoxysilyldodecyl)hexasulfide; 2-benzothiazolyl-(12-triethoxysilyldodecyl)hexasulfide; 2-benzothiazolyl-(18-trimethoxysilyloctadecyl)hexasulfide; 2-benzothiazolyl-(18-methoxydimethylsilyloctadecyl)hexasulfide; 2-benzothiazolyl-(2-trimethoxysilyl-2-methylethyl)hexasulfide; 2-benzothiazolyl-(2-tripropoxysilyl-2-methylethyl)hexasulfide; 2-benzothiazolyl-(2-trioctoxysilyl-2-methylethyl)hexasulfide; 2-benzothiazolyl-(2-trimethoxysilyl-phenyl)hexasulfide; 2-benzothiazolyl-(2-triethoxysilyl-phenyl)hexasulfide; 2-benzothiazolyl-(2-trimethoxysilyl-tolyl)hexasulfide; 2-benzothiazolyl-(2-triethoxysilyl-tolyl)hexasulfide; 2-benzothiazolyl-(2-trimethoxysilyl-methyl tolyl)hexasulfide; 2-benzothiazolyl-(2-triethoxysilyl-methyl tolyl)hexasulfide; 2-benzothiazolyl-(2-trimethoxysilyl-ethyl phenyl)hexasulfide; 2-benzothiazolyl-(2-triethoxysilyl-ethyl phenyl)hexasulfide; 2-benzothiazolyl-(2-trimethoxysilyl-ethyl tolyl)hexasulfide; 2-benzothiazolyl-(2-triethoxysilyl-ethyl tolyl)hexasulfide; 2-benzothiazolyl-(3-trimethoxysilyl-propyl phenyl)hexasulfide; 2-benzothiazolyl-(3-triethoxysilyl-propyl phenyl)hexasulfide; 2-benzothiazolyl-(3-trimethoxysilyl-propyl tolyl)hexasulfide; and 2-benzothiazolyl-(3-triethoxysilyl-propyl tolyl)hexasulfide.

Representative organosilicon polysulfide compounds of formula II where n is 7 which may be prepared in accordance with the present invention include 2-benzothiazolyl-(3-triethoxysilylpropyl)heptasulfide; 2-benzothiazolyl-(2-trimethoxysilylethyl)heptasulfide; 2-benzothiazolyl-(3-trimethoxysilylpropyl)heptasulfide; 2-benzothiazolyl-(2-triethoxysilylpropyl)heptasulfide; 2-benzothiazolyl-(3-triethoxysilylpropyl)heptasulfide; 2-benzothiazolyl-(2-tripropoxysilylethyl)heptasulfide; 2-benzothiazolyl-(2-tri-sec-butoxysilylethyl)heptasulfide; 2-benzothiazolyl-(3-tri-t-butoxysilylethyl)heptasulfide; 2-benzothiazolyl-(3-triisopropoxysilylpropyl)heptasulfide; 2-benzothiazolyl-(3-trioctoxysilylpropyl)heptasulfide; 2-benzothiazolyl-2-[tri(2-ethylhexoxy)silylethyl]heptasulfide; 2-benzothiazolyl-(2-dimethoxy ethoxysilylethyl)heptasulfide; 2-benzothiazolyl-(3-methoxyethoxypropoxysilylpropyl)heptasulfide; 2-benzothiazolyl-(3-dimethoxymethylsilylpropyl)heptasulfide; 2-benzothiazolyl-(3-methoxy dimethylsilylpropyl)heptasulfide; 2-benzothiazolyl-(3-diethoxymethyl-silylpropyl)heptasulfide; 2-benzothiazolyl-(3-ethoxydimethylsilylpropyl)heptasulfide; 2-benzothiazolyl-(3-cyclohexoxy dimethylsilylpropyl)heptasulfide; 2-benzothiazolyl-(4-trimethoxysilylbutyl)heptasulfide; 2-benzothiazolyl-(3-trimethoxysilyl-3-methylpropyl)heptasulfide; 2-benzothiazolyl-(3-tripropoxysilyl-3-methylpropyl)heptasulfide; 2-benzothiazolyl-(3-dimethoxy methylsilyl-3-ethylpropyl)heptasulfide; 2-benzothiazolyl-(3-trimethoxysilyl-2-methylpropyl)heptasulfide; 2-benzothiazolyl-(3-dimethoxyphenylsilyl-2-methylpropyl)heptasulfide; 2-benzothiazolyl-(3-trimethoxysilylcyclohexyl)heptasulfide; 2-benzothiazolyl-(12-trimethoxysilyldodecyl)heptasulfide; 2-benzothiazolyl-(12-triethoxysilyldodecyl)heptasulfide; 2-benzothiazolyl-(18-trimethoxysilyloctadecyl)heptasulfide; 2-benzothiazolyl-(18-methoxydimethylsilyloctadecyl)heptasulfide; 2-benzothiazolyl-(2-trimethoxysilyl-2-methylethyl)heptasulfide; 2-benzothiazolyl-(2-tripropoxysilyl-2-methylethyl)heptasulfide; 2-benzothiazolyl-(2-trioctoxysilyl-2-methylethyl)heptasulfide; 2-benzothiazolyl-(2-trimethoxysilyl-phenyl)heptasulfide; 2-benzothiazolyl-(2-triethoxysilyl-phenyl)heptasulfide; 2-benzothiazolyl-(2-trimethoxysilyl-tolyl)heptasulfide; 2-benzothiazolyl-(2-triethoxysilyl-tolyl)heptasulfide; 2-benzothiazolyl-(2-trimethoxysilyl-methyl tolyl)heptasulfide; 2-benzothiazolyl-(2-triethoxysilyl-methyl tolyl)heptasulfide; 2-benzothiazolyl-(2-trimethoxysilyl-ethyl phenyl)heptasulfide; 2-benzothiazolyl-(2-triethoxysilyl-ethyl phenyl)heptasulfide; 2-benzothiazolyl-(2-trimethoxysilyl-ethyl tolyl)heptasulfide; 2-benzothiazolyl-(2-triethoxysilyl-ethyl tolyl)heptasulfide; 2-benzothiazolyl-(3-trimethoxysilylopropyl phenyl)heptasulfide; 2-benzothiazolyl-(3-triethoxysilyl-propyl phenyl)heptasulfide; 2-benzothiazolyl-(3-trimethoxysilyl-propyl tolyl)heptasulfide; and 2-benzothiazolyl-(3-triethoxysilyl-propyl tolyl)heptasulfide.

Representative organosilicon polysulfide compounds of formula II where n is 8 which may be prepared in accordance with the present invention include 2-benzothiazolyl-(3-triethoxysilylpropyl)octasulfide; 2-benzothiazolyl-(2-trimethoxysilylethyl)octasulfide; 2-benzothiazolyl-(3-trimethoxysilylpropyl)octasulfide; 2-benzothiazolyl-(2-triethoxysilylpropyl)octasulfide; 2-benzothiazolyl-(3-triethoxysilylpropyl)octasulfide; 2-benzothiazolyl-(2-tripropoxysilylethyl)octasulfide; 2-benzothiazolyl-(2-tri-sec-butoxysilylethyl)octasulfide; 2-benzothiazolyl-(2-tri-t-butoxysilylethyl)octasulfide; 2-benzothiazolyl-(3-triisopropoxysilylpropyl)octasulfide; 2-benzothiazolyl-(3-trioctoxysilylpropyl)octasulfide; 2-benzothiazolyl-2-[tri(2-ethylhexoxy)silylethyl]octasulfide; 2-benzothiazolyl-(2-dimethoxy ethoxysilylethyl)octasulfide; 2-benzothiazolyl-(3-methoxyethoxypropoxysilylpropyl)octasulfide; 2-benzothiazolyl-(3-dimethoxymethylsilylpropyl)octasulfide; 2-benzothiazolyl-(3-methoxy dimethylsilylpropyl)octasulfide; 2-benzothiazolyl-(3-diethoxymethyl-silylpropyl)octasulfide; 2-benzothiazolyl-(3-ethoxydimethylsilylpropyl)octasulfide; 2-benzothiazolyl-(3-cyclohexoxy dimethylsilylpropyl)octasulfide; 2-benzothiazolyl-(4-trimethoxysilylbutyl)octasulfide; 2-benzothiazolyl-(3-trimethoxysilyl-3-methylpropyl)octasulfide; 2-benzothiazolyl-(3-tripropoxysilyl-3-methylpropyl)octasulfide; 2-benzothiazolyl-(3-dimethoxy methylsilyl-3-ethylpropyl)octasulfide; 2-benzothiazolyl-(3-trimethoxysilyl-2-methylpropyl)octasulfide;

2-benzothiazolyl-(3-dimethoxyphenylsilyl-2-methylpropyl) octasulfide; 2-benzothiazolyl-(3-trimethoxysilylcyclohexyl) octasulfide; 2-benzothiazolyl-(12-trimethoxysilyldodecyl) octasulfide; 2-benzothiazolyl-(12-triethoxysilyldodecyl) octasulfide; 2-benzothiazolyl-(18-trimethoxysilyloctadecyl) octasulfide; 2-benzothiazolyl-(18-methoxydimethylsilyloctadecyl)octasulfide; 2-benzothiazolyl-(2-trimethoxysilyl-2-methylethyl) octasulfide; 2-benzothiazolyl-(2-tripropoxysilyl-2-methylethyl)octasulfide; 2-benzothiazolyl-(2-trioctoxysilyl-2-methylethyl)octasulfide; 2-benzothiazolyl-(2-trimethoxysilyl-phenyl)octasulfide; 2-benzothiazolyl-(2-triethoxysilyl-phenyl)octasulfide; 2-benzothiazolyl-(2-trimethoxysilyl-tolyl)octasulfide; 2-benzothiazolyl-(2-triethoxysilyl-tolyl)octasulfide; 2-benzothiazolyl-(2-trimethoxysilyl-methyl tolyl)octasulfide; 2-benzothiazolyl-(2-triethoxysilyl-methyl tolyl)octasulfide; 2-benzothiazolyl-(2-trimethoxysilyl-ethyl phenyl)octasulfide; 2-benzothiazolyl-(2-triethoxysilyl-ethyl phenyl)octasulfide; 2-benzothiazolyl-(2-trimethoxysilyl-ethyl tolyl)octasulfide; 2-benzothiazolyl-(2-triethoxysilyl-ethyl tolyl)octasulfide; 2-benzothiazolyl-(3-trimethoxysilyl-propyl phenyl) octasulfide; 2-benzothiazolyl-(3-triethoxysilyl-propyl phenyl)octasulfide; 2-benzothiazolyl-(3-trimethoxysilyl-propyl tolyl)octasulfide; and 2-benzothiazolyl-(3-triethoxysilyl-propyl tolyl)octasulfide.

The desired products are prepared by reacting the benzothiazolyl-morpholinyl disulfide compound of formula III with a mercapnoalkoxysilane compound of formula IV. Representative examples of compounds of formula IV include 2-mercaptoethyl trimethoxysilane, 3-mercaptopropyl trimethoxysilane, 3-mercaptopropyl triethoxysilane, 2-mercaptopropyl triethoxysilane, 2-mercaptoethyl tripropoxysilane, 2-mercaptoethyl tri sec-butoxysilane, 3-mercaptopropyl tri-t-butoxysilane, 3-mercaptopropyl triisopropoxysilane; 3-mercaptopropyl trioctoxysilane, 2-mercaptoethyl tri(2-ethylhexoxy)silane, 2-mercaptoethyl dimethoxy ethoxysilane, 3-mercaptopropyl methoxyethoxypropoxysilane, 3-mercaptopropyl dimethoxy methylsilane, 3-mercaptopropyl menhoxy dimethylsilane, 3-mercaptopropyl ethoxy dimethylsilane, 3-mercaptopropyl diethoxy methylsilane, 3-mercaptopropyl cyclohexoxy dimethyl silane, 4-mercaptobutyl trimethoxysilane, 3-mercapto-3-methylpropyltrimethoxysilane, 3-mercapto-3-methylpropyl-tripropoxysilane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyl-tripropoxysilane, 2-mercapto-2-methylethyl-trioctoxysilane, 2-mercaptophenyl trimethoxysilane, 2-mercaptophenyl triethoxysilane; 2-mercaptotolyl trimethoxysilane; 2-mercaptotolyl triethoxysilane; α-mercaptomethyltolyl trimethoxysilane; α-mercaptomethyltolyl triethoxysilane; 2-mercaptoethylphenyl trimethoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

The molar ratio of the compound of formula III to the compound of formula IV may range from 1:5 to 5:1. Preferably, the molar ratio ranges from 1:3 to 3:1 with a range of from 1:1 to 2:1 being particularly preferred.

The reaction should be conducted in the absence of appreciable amounts of water because the presence of an alkoxysilane moiety may be hydrolysed by contact with water.

The reaction of the present invention may be conducted in the presence of an organic solvent. Suitable solvents which may be used include chloroform, dichloromethane, carbon tetrachloride, hexane, heptane, cyclohexane, xylene, benzene, dichloroethylene, trichloroethylene, dioxane, diisopropyl ether, tetrahydrofuran and toluene. As indicated above, care should be exercised to avoid the presence of water during the reaction. Therefore, none of the above solvent should contain any appreciable levels of water. Preferably, the organic solvent is chloroform, heptane, cyclohexane, xylene and toluene.

The reaction may be conducted over a variety of temperatures. Generally speaking, the reaction is conducted in a temperature ranging from 20° C. to 140° C. Preferably, the reaction is conducted at a temperature ranging from 20° C. to 90° C.

The process of the present invention may be conducted at a variety of pressures. Generally speaking, however, the reaction is conducted at a pressure ranging from 0.096 to 4.83 kg/cm².

EXAMPLE 1

Preparation of a Mixture of Organosilicon Polysulfide Compounds

A 1-quart (0.945 liter) glass reactor was charged with 200 ml of toluene, 23.8 g (0.10 mole) of 3-mercaptopropyltriethoxysilane and 25.5 g (0.10 mole) of 4-morpholinyl-2-benzothiazolyl disulfide. The reactor was flushed with nitrogen and stirred for ½ hour. The reactants were then allowed to set overnight at room temperature. The precipitate that formed was filtered and the resulting solution was stripped of solvent and morpholine at reduced pressure (29 in. of Hq. @ 50° C.) to give 24.7 g of thick amber-colored liquid. Mass spectrometry analysis shows the liquid product mixture was composed of 80 percent by area of the reaction products conforming to formula I where each $R^1$ was an unsubstituted alkylene group having a total of 3 carbon atoms, each Z is of the formula:

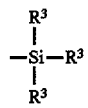

each $R^3$ was an alkoxy group having 2 carbon atoms and the breakdown of each product of formula I as to n was as follows:

| n | % by area |
|---|---|
| $S_2$ | 55 |
| $S_3$ | 18 |
| $S_4$ | 17 |
| $S_5$ | 7 |
| $S_6$ | 1 |
| $S_7$ | <1 |
| $S_8$ | <1 |

20 percent by area of the reaction product conforming to formula II, where $R^1$ was an unsubstituted alkylene group having a total of 3 carbon atoms, each Z was of the formula:

$$-\underset{\underset{R^3}{|}}{\overset{\overset{R^3}{|}}{Si}}-R^3$$

where each $R^3$ was an alkoxy group having 2 carbon atoms and the breakdown of each product of formula II as to n was as follows:

| n | % by area |
|---|---|
| $S_2$ | 86 |
| $S_3$ | 12 |
| $S_4$ | 3 |
| $S_5$ | <1 |
| $S_6$ | <1 |

EXAMPLE 2

Preparation of a Mixture of Organosilicon Polysulfide Compounds

A reaction was carried out under the same conditions of Example 1 except 114.0 g (0.4 mole) of 4-morpholinyl-2-benzothiazolyl disulfide and 47.6 g (0.20 mole) of 3-mercaptopropyltriethoxysilane were added to the reactor in 800 ml of toluene. Mass spectrometry analysis shows the liquid product mixture was composed of 67 percent by area of the reaction products conforming to formula I where each $R^1$ was an unsubstituted alkylene group having a total of 3 carbon atoms, each Z is of the formula:

$$-\underset{\underset{R^3}{|}}{\overset{\overset{R^3}{|}}{Si}}-R^3$$

each $R^3$ was an alkoxy group having 2 carbon atoms and the breakdown of each product of formula I as to n was as follows:

| n | % by area |
|---|---|
| $S_2$ | 39 |
| $S_3$ | 18 |
| $S_4$ | 22 |
| $S_5$ | 18 |
| $S_6$ | 3 |

33 percent by area of the reaction product conforming to formula II, where $R^1$ was an unsubstituted alkylene group having a total of 3 carbon atoms, each Z was of the formula:

$$-\underset{\underset{R^3}{|}}{\overset{\overset{R^3}{|}}{Si}}-R^3$$

where each $R^3$ was an alkoxy group having 2 carbon atoms and the breakdown of each product of formula II as to n was as follows:

| n | % by area |
|---|---|
| $S_2$ | 84 |
| $S_3$ | 12 |
| $S_4$ | 4 |

What is claimed is:

1. A process for the preparation of organosilicon polysulfide compounds comprising reacting (a) a benzothiazolyl-morpholinyl disulfide compound of the formula $$\text{O}\underset{\diagdown}{\overset{\diagup}{\diagdown}}\text{N}-\text{S}-\text{S}-\text{C}\underset{\text{S}}{\overset{\text{N}}{\diagdown}}\diagup\diagdown \qquad \text{III}$$

with (b) mercaptoalkoxysilane compound of the formula $$Z-R^1-SH \qquad \qquad IV$$

wherein Z is selected from the group consisting of $$-\underset{\underset{R^3}{|}}{\overset{\overset{R^2}{|}}{Si}}-R^2, \quad -\underset{\underset{R^3}{|}}{\overset{\overset{R^2}{|}}{Si}}-R^3 \quad \text{and} \quad -\underset{\underset{R^3}{|}}{\overset{\overset{R^3}{|}}{Si}}-R^3$$

wherein $R^1$ is selected from the group consisting of a substituted or unsubstituted alkylene group having a total of 1 to 18 carbon atoms and a substituted or unsubstituted arylene group having a total of 6 to 12 carbon atoms; $R^2$ may be the same or different and is independently selected from the group consisting of an alkyl group having 1 to 18 carbons and phenyl; and $R^3$ may be the same or different and is independently selected from the group consisting of alkoxy groups having 1 to 8 carbon atoms and cycloalkoxy groups with 5 to 8 carbon atoms.

2. The process of claim 1 wherein

Z is $$-\underset{\underset{R^3}{|}}{\overset{\overset{R^3}{|}}{Si}}-R^3,$$

$R^1$ is an alkylene group having 2 to 3 carbon atoms and $R^3$ selected from the group consisting of alkoxy groups having 1 to 3 carbon atoms.

3. The process of claim 1 wherein the molar ratio of the compound of formula III to the compound of formula IV ranges from 1:5 to 5:1.

4. The process of claim 3 wherein the molar ratio of the compound of formula III to the compound of formula IV ranges from 1:3 to 3:1.

5. The process of claim 1 wherein said organosilicon disulfide compounds are of the formula:

$$Z-R^1-S_n-R^1-Z \qquad \qquad I$$

and

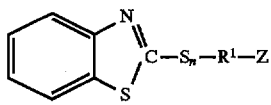
II wherein Z is selected from the group consisting of

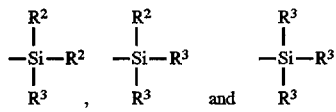

wherein $R^1$ is selected from the group consisting of a substituted or unsubstituted alkylene group having a total of 1 to 18 carbon atoms and a substituted or unsubstituted arylene group having a total of 6 to 12 carbon atoms; and n is an integer of from 2 to 8; $R^2$ may be the same or different and is independently selected from the group consisting of an alkyl group having 1 to 18 carbons and phenyl; $R^3$ may be the same or different and is independently selected from the group consisting of alkoxy groups having 1 to 8 carbon atoms and cycloalkoxy groups with 5 to 8 carbon atoms; and n is an integer of from 2 to 8.

6. The process of claim 1 wherein $R^1$ is an unsubstituted alkylene group having a total of from 2 to 5 carbon atoms.

7. The process of claim 1 wherein z is

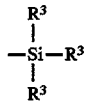

and each $R^3$ is an alkoxy group having from 1 to 3 carbon atoms.

8. The process of claim 5 wherein $R^1$ is an unsubstituted alkylene group having a total of from 2 to 5 carbon atoms.

9. The process of claim 1 wherein n is an integer of from 2 to 6.

10. The process of claim 1 wherein z is

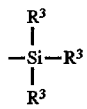

and each $R^3$ is an alkoxy group having from 1 to 3 carbon atoms.

11. The process of claim 1 wherein said reaction is in absence of water and in the presence of an organic solvent selected from the group consisting of chloroform, dichloromethane, carbon tetrachloride, hexane, heptane, cyclohexane, xylene, benzene, dichloroethylene, trichloroethylene, dioxane, diisopropyl ether, tetrahydrofuran and toluene.

12. The process of claim 1 wherein the reaction is conducted at a temperature ranging from 20° C. to 140° C.

13. The process of claim 12 wherein the reaction is conducted at a temperature ranging from 20° C. to 90° C.

14. The process of claim 1 wherein the reaction is conducted at a pressure ranging from 0.096 to 4.83 kg/cm².

* * * * *